United States Patent
Klinkhammer

[11] Patent Number: 5,224,764
[45] Date of Patent: Jul. 6, 1993

[54] TOOTH CLEANING DEVICE AND METHOD FOR MAKING THE SAME

[76] Inventor: Ronald W. Klinkhammer, 10231 63rd Ave. South, Seattle, Wash. 98178

[21] Appl. No.: 978,712

[22] Filed: Nov. 19, 1992

Related U.S. Application Data

[63] Continuation of Ser. No. 499,022, Mar. 26, 1990, Pat. No. 5,171,066, which is a continuation-in-part of Ser. No. 145,771, Jan. 19, 1988, abandoned.

[51] Int. Cl.⁵ .............................................. A46D 3/00
[52] U.S. Cl. ...................................................... 300/21
[58] Field of Search .......................... 300/21; 264/243; 425/805; 15/167.2

[56] References Cited

U.S. PATENT DOCUMENTS

| | | |
|---|---|---|
| 1,967,783 | 7/1934 | Rudof .................................... 300/21 |
| 2,621,369 | 12/1952 | Gantz et al. ...................... 300/21 X |
| 2,783,490 | 3/1957 | Kutik ................................. 300/21 X |
| 4,691,705 | 9/1987 | Reed ..................................... 264/243 |
| 5,114,214 | 5/1992 | Barman ................................. 300/21 |

FOREIGN PATENT DOCUMENTS 8707123 12/1987 World Int. Prop. O. ............ 300/21

*Primary Examiner*—Douglas D. Watts
*Attorney, Agent, or Firm*—Christopher Duffy

[57] ABSTRACT

The device is improved over earlier versions in providing for the wings of the device maintaining the angular relationship therebetween when the reciprocate crosswise of the space between the arms to accommodate to variance in the diameter of the teeth. It is also improved in providing an implement which is cast about the arms to enwrap them in more sanitary fashion; and in providing a technique for casting the implement in a way which injects a harder casting material into the cores of the bristle.

7 Claims, 7 Drawing Sheets

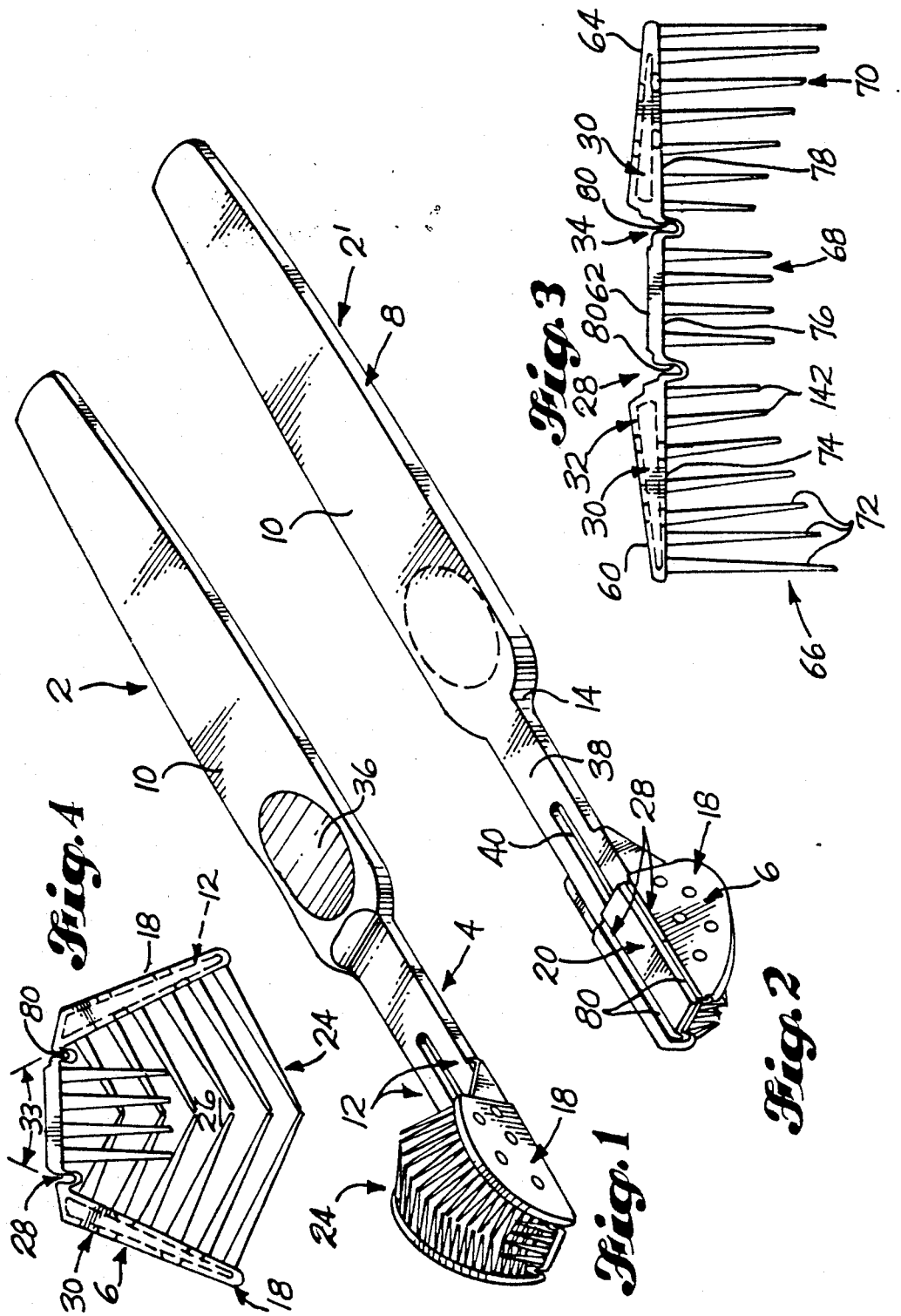

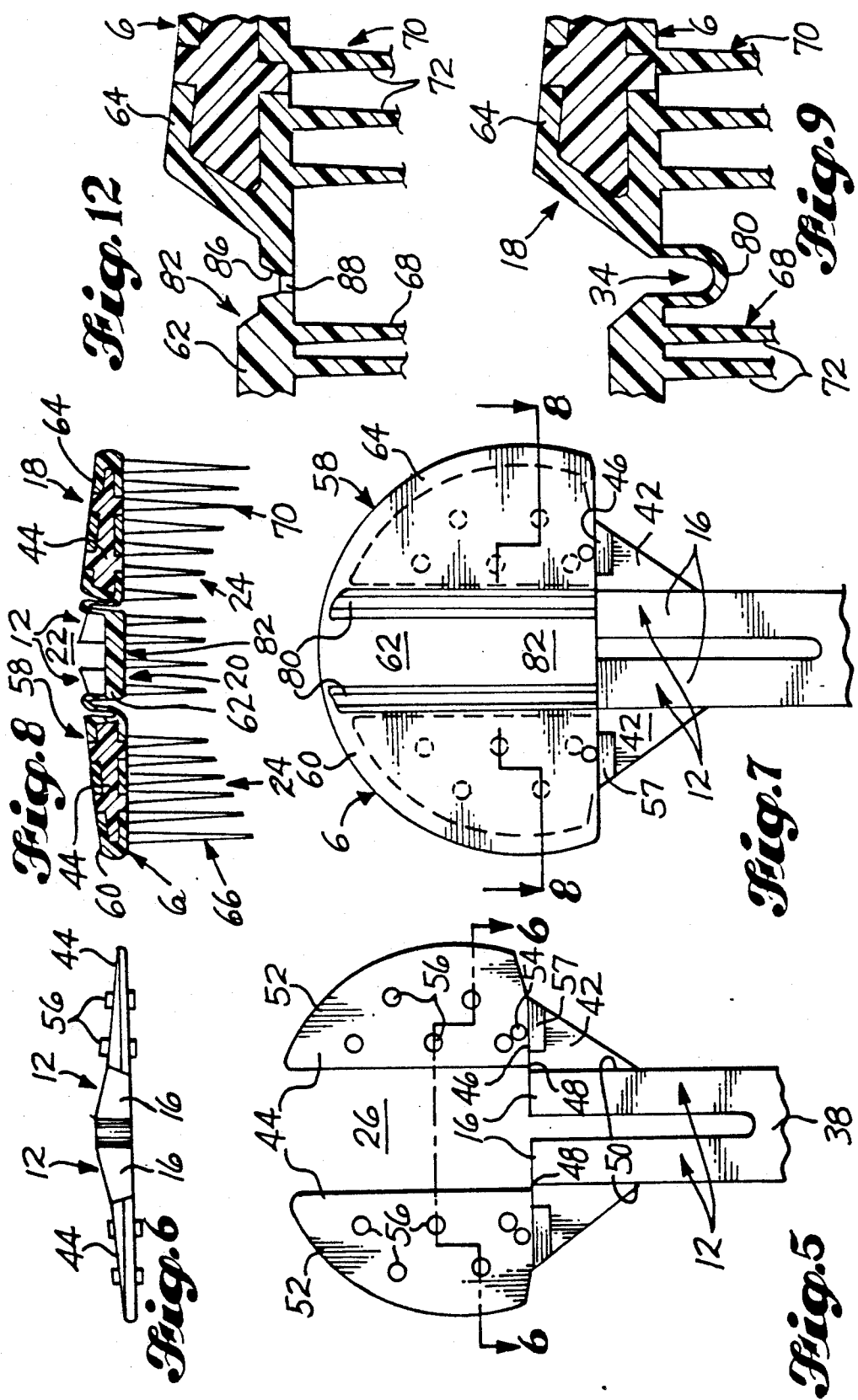

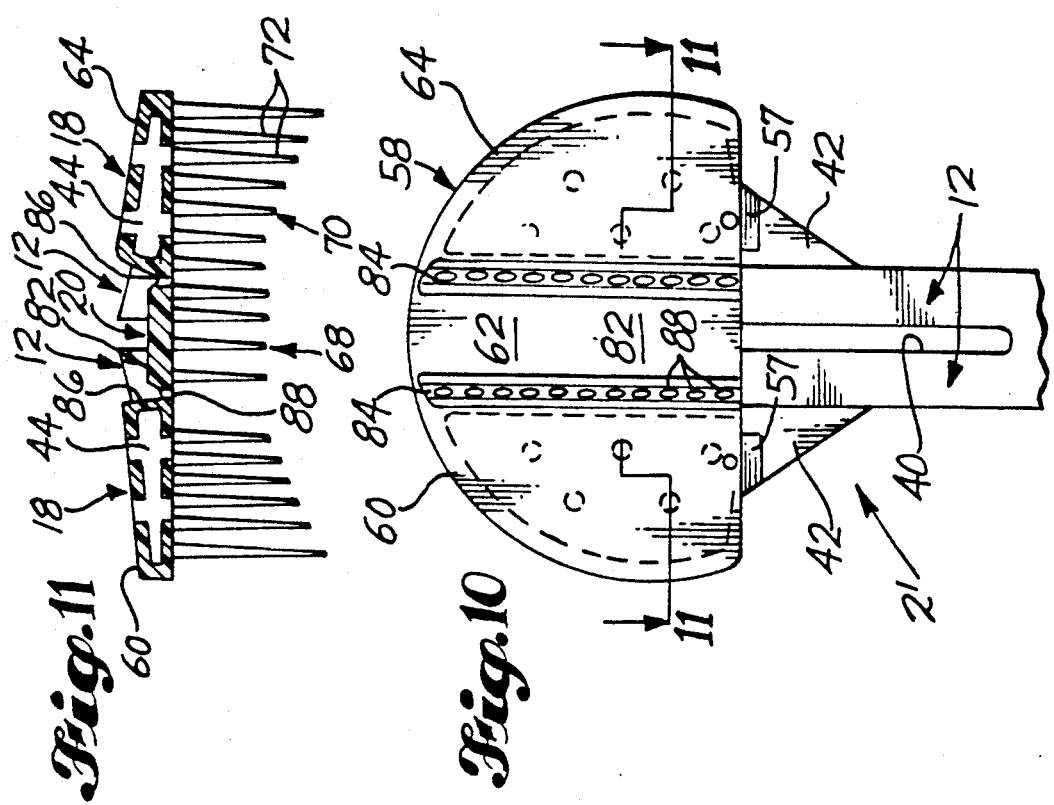

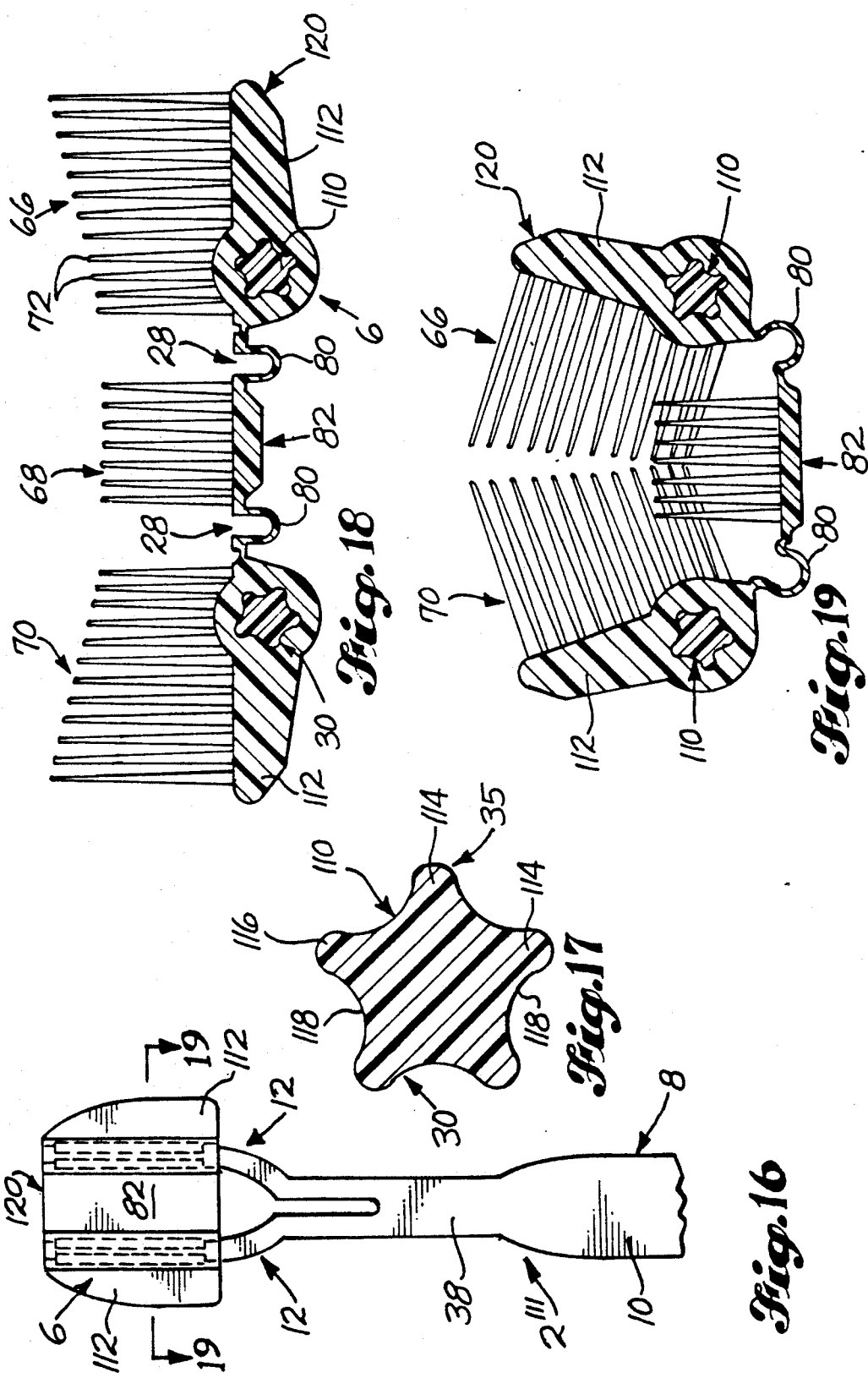

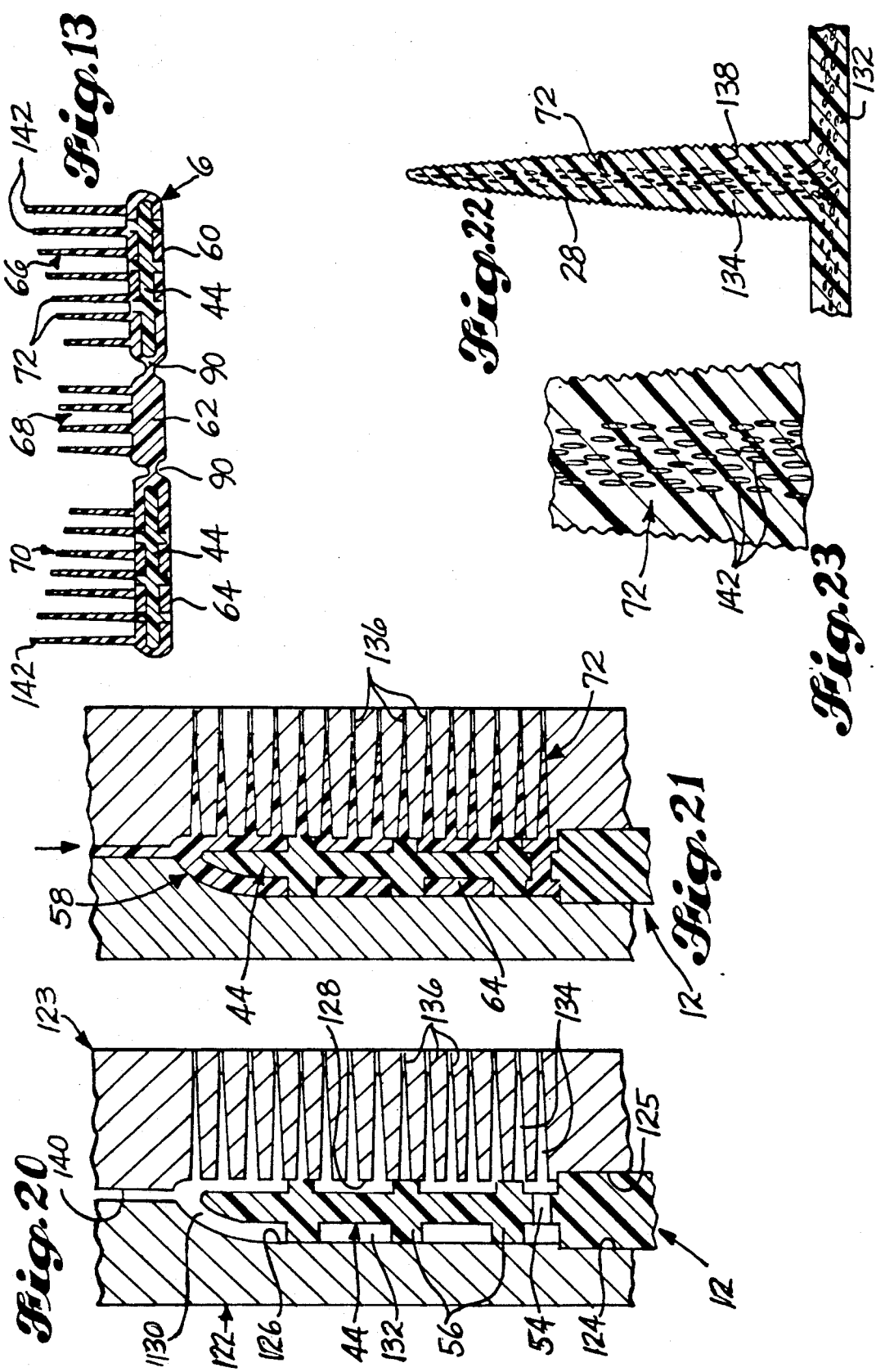

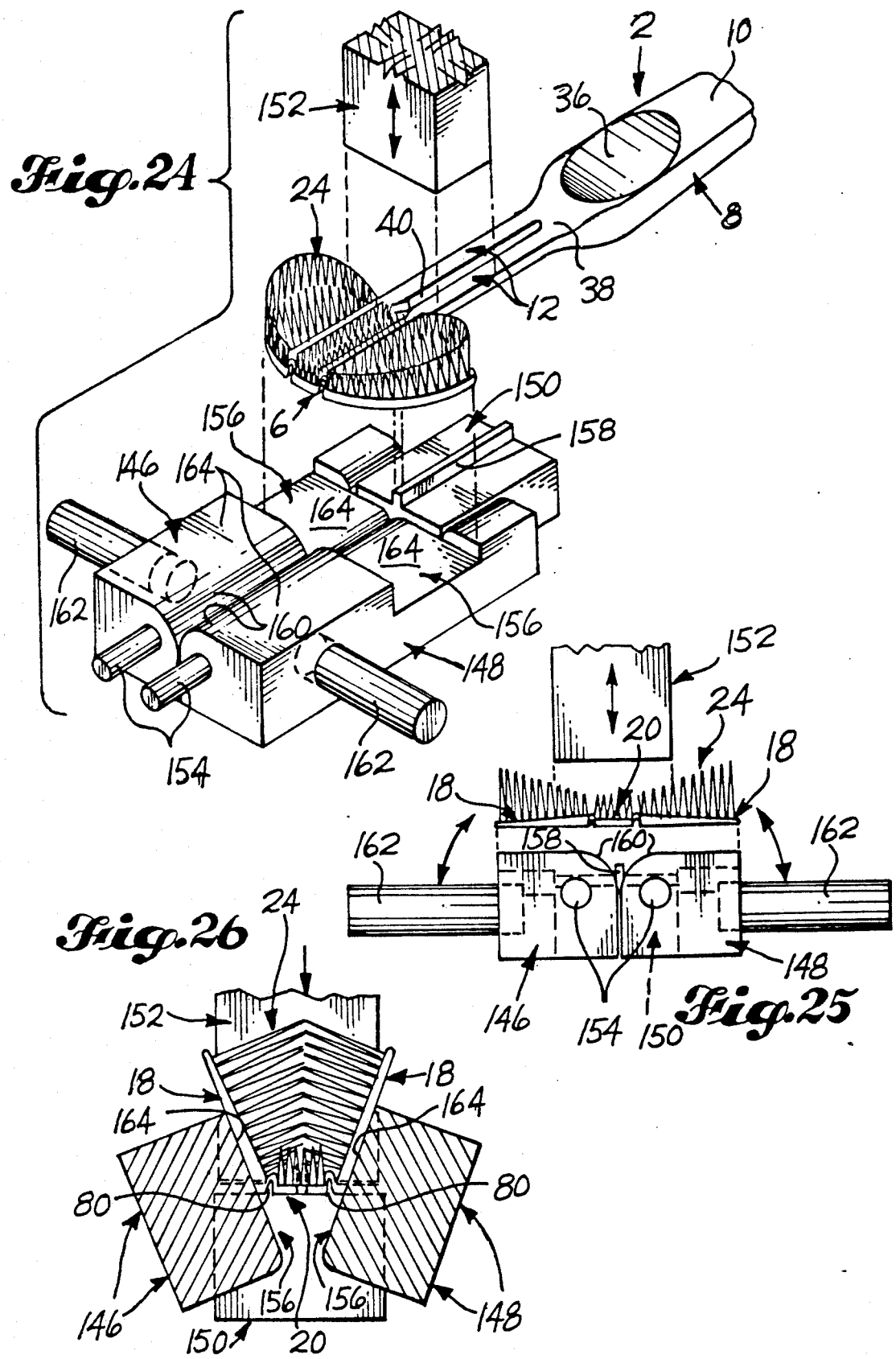

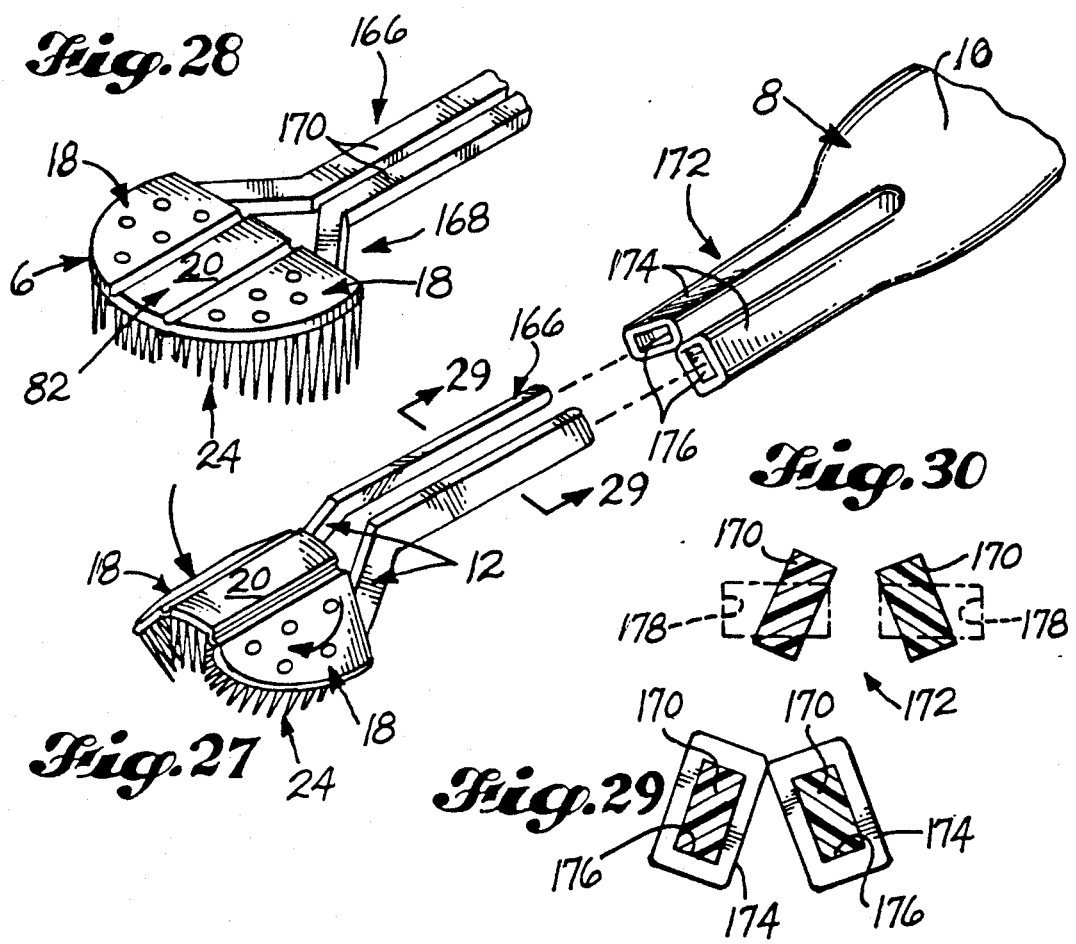
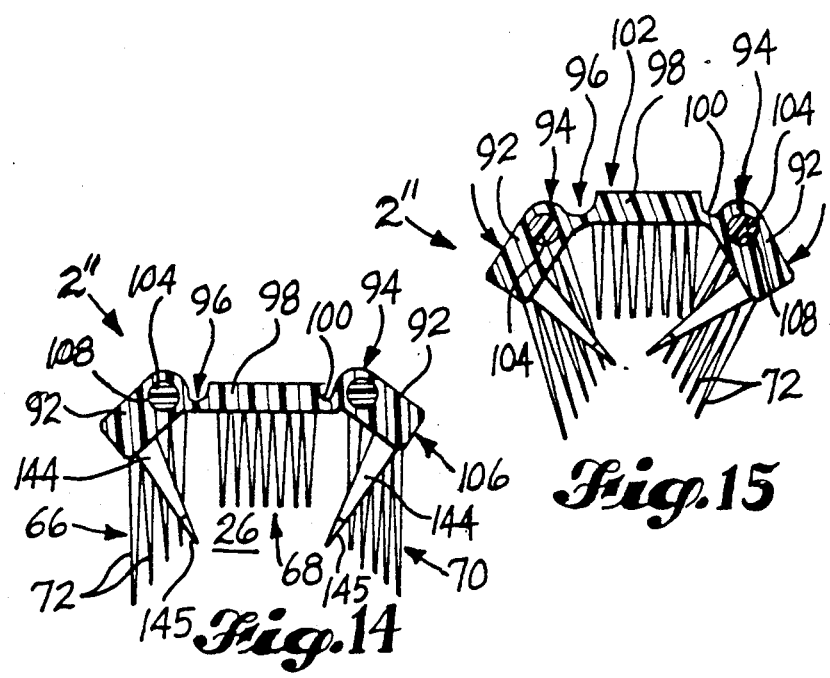

TOOTH CLEANING DEVICE AND METHOD FOR MAKING THE SAME

RELATED APPLICATION

The present application is a continuation of co-pending application Ser. No. 499,022 filed on Mar. 26, 1990 and having the same title, which was a continuation-in-part of Ser. No. 145,771 filed Jan. 19, 1988 now abandoned.

TECHNICAL FIELD

This invention relates to a tooth cleaning device and a method for making the device, and in particular, to a device, and a method for making the same, of the straddle type described in application Ser. No. 145,771 which was filed Jan. 19, 1988 under the title TOOTH CLEANING DEVICE AND METHOD, and is co-pending with the present Application. The present Application is also a continuation-in-part of that Application, and the earlier Application is hereby incorporated in the present application by this reference to it.

BACKGROUND ART

The earlier Application disclosed a tooth cleaning device having carrier means which were operatively supported on elongated means, including a handle, for positioning the carrier means adjacent a row of teeth in the mouth of the user, and which comprised a pair of spaced, coplanar arms that operatively projected from the distal end of the positioning means and were resiliently flexible in the plane of the arms at points operatively spaced outboard from the distal end of the positioning means. A tooth cleaning implement was supported on the arms at the aforesaid points, for application to the user's teeth while the carrier means were supported adjacent the row of the same, but contrary to the prior art, the tooth cleaning implement comprised a pair of spaced wings and a midsection in the space therebetween, and the wings were relatively flexibly interconnected with the midsection and had tooth cleaning means on corresponding sides thereof. Moreover, the implement was operatively interconnected with the respective arms at the wings thereof, so that the aforesaid tooth cleaning sides of the wings are opposed to one another in the space between the arms, and the midsection of the implement was supported on the wings, independent of the arms, to give the implement a taco shell-shaped configuration in which the wings had a predetermined angular relationship therebetween and were capable of flexing in conjunction with the arms at the pair of flexible connections between the midsection and the respective wings. Furthermore, there were leveraging means in one of the pair of connections between the arms and the wings, and the pair of connections between the midsection and the respective wings, whereby when the implement was straddled about the row of teeth and translated along the row opposite the inside and outside faces of the teeth, the implement retained the aforesaid configuration, yet the wings of the same were capable of reciprocating in relation to one another crosswise of the space between the arms to accommodate to variance in the diameter of the teeth.

DISCLOSURE OF THE INVENTION

When the wings reciprocate for this purpose, crosswise of the space between the arms, it is desirable that the wings maintain the same angular relationship as was given them when the implement was straddled about the row of teeth. That is, once the angular relationship has been established through the choice of brush, brush size, or grip, it is desirable that the wings maintain that same angular relationship from one tooth to the next. Otherwise, the wings will scrub one tooth with a full broadside application of the tooth cleaning means thereon, and then scrub the next tooth will less than a full broadside application of the tooth cleaning means, because as the angular relationship of the wings varies, the tooth cleaning means will be tilted toward or away from the faces of the teeth, and will no longer be applied broadside of them.

The present invention constitutes a further improvement over even that of the earlier device, in that linkage means are provided in the flexible connections between the wings and the midsection whereby when the pairs of arms and wings reciprocate in conjunction with one another, crosswise of the space between the arms, the midsection responds to the reciprocation by reciprocating along perpendiculars to the plane of the arms to substantially preserve the angular relationship between the wings. Accordingly, the inventive device is now not only capable of accommodating to variance in tooth diameter, but also of maintaining the angular relationship between the wings as it does so. The device is also capable of providing a vertical component to the cleaning action of the tooth cleaning means, if desired, since the arms may also be resiliently flexible along perpendiculars to the plane of the arms, and if so, with the linkage means provided, the pairs of arms and wings are now capable of being reciprocated in opposite directions, relative to the plane of the arms, to generate the vertical component.

The improved device has many embodiments, including one group of first-line embodiments in which the pairs of arms and wings are interlocked against relative rotation at the connections therebetween, and the leveraging means are formed in the connections between the arms and wings; another group in which the pairs of arms and wings are interengaged for relative rotation at the connections therebetween, and the leveraging means are formed in the flexible connections between the midsection and wings of the implement; and still a third group in which the pairs of arms and wings are interengaged for relative rotation at the connections therebetween, but the rotary connections have means therein whereby the arms and wings can be fixed against relative rotation at angular intervals thereabout, the leveraging means being formed in the rotary connections at the respective intervals.

In the first mentioned group of first-line embodiments wherein the pairs of arms and wings are interlocked, certain of the embodiments are equipped with arms that have laterally projecting tenons thereon, and the wings of the implement are interconnected with the tenons to form tenon and mortise joints in the connections between the arms and wings. For example, in some of these, the tenons take the form of clapper-shaped jaws on the distal ends of the arms, and the wings are interconnected with the clapper-shaped jaws of the arms to form tenon and mortise joints in the connections between the arms and wings.

Furthermore, in the first mentioned group of first-line embodiments, certain of them are equipped with flexible connections between the midsection and the respective wings, which have pleat-like linkages therein whereby the midsection can reciprocate along perpendiculars to the arms as part of an extensible and contractible expansion joint in the space between the arms. In one subgroup, the implement has a hammock-like cowling therein, comprising three relatively flexibly interconnected sections arranged in a row crosswise of the arms, the endmost sections of which are interconnected with the arms as the wings of the implement, and the midsection of which is suspended in the space between the arms by the pair of flexible connections between the midsection and the endmost sections of the cowling. In some embodiments of the subgroup, the linkages take the form of webs of flexible and/or pliable sheet material which have reentrantly folded pleats therein, croswide the length of the row of cowling sections. In others, the linkages take the form of webs of flexible and/or pliable sheet material which have reduced diameter thicknesses, relative to the midsection and wings of the cowling, and are resiliently stretchable lengthwise the row of cowling sections. In certain of the latter, moreover, the webs of sheet material have rows of perforations therein, crosswide the length of the row of cowling sections.

In the second mentioned group of first-line embodiments wherein the pairs of arms and wings are interengaged for relative rotation at the connections therebetween, some of the group are equipped with flexible connections between the midsection and the respective wings of the implement, which have relatively articulated linkages therein whereby the midsection can reciprocate linkages perpendiculars to the plane of the arms as part of an extensible and contractible toggle joint between the arms. Once again, in certain of them, the implement has the aforedescribed hammock-like cowling, and the linkages take the form of webs of flexible and/or pliable sheet material which have reduced diameter thicknesses, relative to the midsection and wings of the cowling, but are relatively stiff lengthwise the row of cowling sections, to perform as toggle links in the flexible connections.

In the third mentioned group of first-line embodiments wherein the pairs of arms and wings are relatively rotatable, but can be fixed against relative rotation at angular intervals thereabout, certain of the embodiments are equipped with arms which have laterally projecting detents thereon, but the bodies of the wings of the implement are sufficiently deformable to be rotatable about the arms, from one detent to the next. In this group, moreover, certain of the embodiments are equipped with flexible connections between the midsection and the respective wings of the implement, which once again have pleat-like linkages therein whereby the midsection can reciprocate along perpendiculars to the plane of the arms as part of an extensible and contractible expansion joint in the space between the arms, as was described for the first mentioned group of first-line embodiments earlier.

The present invention also constitutes an improvement over even that of the earlier device in that in certain embodiments, it is essentially free of crevices and the like at the aforesaid points where the implement is supported on the arms. In this way, it is more sanitary and more readily cleanable after use. According to the invention, the arms in one major group of embodiments are substantially parallel to one another at the aforesaid points thereon. A tooth cleaning implement is supported on the arms at the aforesaid points, having a monolithic hammock-like cowling therein comprising three relatively flexibly interconnected sections arranged in a row crosswise of the arms. The endmost sections of the monolithic cowling have sockets therein that are engaged about the arms to form spigot and socket connections therebetween, and the midsection of the cowling is suspended in the space between the arms by the pair of flexible connections between the midsection and the endmost sections of the cowling. Once again, the aforementioned groups of first-line embodiments are provided in connection with this latter mentioned group as well, and in those where the arms and endmost sections of the cowling are interlocked against relative rotation at the spigot and socket connections therebetween, the leveraging means may be encased within the connections for sanitary reasons, as for example, where the arms have laterally projecting tenons thereon, and the endmost sections of the cowling are encased glove-tight around the tenons, to form tenon and mortise joints in the spigot and socket connections. In fact, the arms may have substantially parallel terminal portions on the distal ends thereof, the tenons may project from the terminal portions of the arms, and the endmost sections of the cowling may be encased glove-tight around both the tenons and terminal portions of the arms, to form tenon and mortise joints in which the arms are fully enwrapped by the cowling at the aforesaid points where the implement is supported thereon. Meanwhile, the same is also true where the pairs of arms and endmost sections are interengaged for relative rotation, or for relative rotation, but with means in the rotary connections whereby they can be fixed against relative rotation at angular intervals thereabout. In each instance, the arms may be fully enwrapped by the cowling at the points where it is supported on the arms.

Often, the monolithic cowling is made of plastic resin material, and the endmost sections of the cowling have elongated tooth brushing bristle on corresponding sides thereof, which are monolithic with the cowling. Moreover, the bristle on the respective sides of the endmost sections are often individually discrete, and spaced apart from one another along each side. They may also have cores of relatively hard material, and sheaths of relatively softer material surrounding the same; and they may have bodies which taper inwardly of their respective longitudinal axes, in the directions relatively outward from the respective sides of the endmost sections. And furthermore, they may have textured surfaces on the exteriors thereof, and barbs on the tips thereof.

The midsection of the cowling may also have elongated tooth brushing bristle on the same side thereof.

The invention also includes an improved method for making a tooth brushing implement which is to be supported by a pair of spaced coplanar arms in the tooth brushing device. According to the invention, the arms are arranged in a mold cavity so as to be spaced apart from one another in a plane of the cavity, and in addition, they are supported in spaced relationship to those walls of the cavity which are disposed on the opposing sides of the plane. Elongated bristle forming branches of the cavity are formed in one of the walls, and a mass of plastic resin material is injected into the cavity, and any gas in the resin material is vented through the branches of the cavity while the resin mass occupies the cavity and is charged into the branches to form a monolithic cowling of the resin material having the aforedescribed sectional construction in which the endmost sections have the arms encased glove-tight therein, and bristle relatively upstanding on corresponding sides thereof.

In certain embodiments of the method, the arms have studs outstanding on the sides thereof which face the walls of the cavity, and the walls of the cavity are defined by a pair of relatively reciprocable members which are clamped together at the sides of the arms so that the arms are supported in spaced relationship to the walls of the cavity by the studs. Commonly, the gas is vented at the tips of the branches, and the branches are tapered relatively inwardly of the longitudinal axes thereof, in the direction relatively outward of the cavity, to form the aforedescribed bristle for the implement. Often, the branches may also have means on the walls thereof for texturing the exterior surfaces of the bristle, as indicated earlier, and in one group of embodiments, the branches are formed by an electric discharge machine for this purpose.

In some embodiments of the method, the branches are tapered relatively inward of the longitudinal axes thereof, in the direction relatively outward of the cavity, and elongated rods of a relatively higher melting temperature resin material are added to the mass of resin material, for entrainment in the resin charged to the branches when the gas is vented at the tips of the branches, to form relatively harder cores in the bristle of the cowling along the longitudinal axes of the branches.

Where the implement is to be given a taco shell-shaped configuration in the device, the method commonly further comprises the step of reentrantly folding the endmost sections of the cowling about the midsection thereof to form the required configuration.

The invention also includes an improved method for making a tooth brushing device of the type wherein a tooth brushing implement is formed on corresponding end portions of a pair of spaced coplanar arms, spaced prongs are formed on the opposing end portions of the arms, and the prongs are bayonetted into a pair of spaced sockets in the distal end of a tool having a handle for positioning the implement adjacent a row of teeth in the mouth of the user. According to the invention, the implement is foldable and mounted on the arms to bridge therebetween, the prongs are rotated into a gable-like angular relationship to reentrantly fold the implement into a taco shell-shaped configuration, and the prongs are bayonetted into a complimentary pair of gable-like angularly related sockets in the distal end of the tool, to preserve the configuration of the implement while it is positioned adjacent the row of teeth. In certain embodiments, the prongs are initially bayonetted into a pair of coplanar sockets in the distal end of the tool, when the implement is initially mounted in the unfolded condition on the arms, and then the arms are removed from the coplanar sockets and the arms and implement are rotated and folded, respectively, and then bayonetted into the pair of angularly related sockets at the prongs when the device is put to use.

BRIEF DESCRIPTION OF THE DRAWINGS

These features will be better understood by reference to the accompanying drawings wherein several of the foregoing embodiments of the invention are illustrated.

In the drawings:

FIG. 1 is a perspective view of the underside of a tooth brushing tool in which the arms of the tool and the and wings of the implement are interlocked against relative rotation, and the leveraging means are formed in the connections therebetween;

FIG. 2 is a perspective view of the tool at the top thereof;

FIG. 3 is a front elevational view of the tooth brushing implement employed on the tool, when the implement is in the initial unfolded condition thereof prior to straddle-type usage of it;

FIG. 4 is a similar view of the implement when it has been reentrantly folded into a taco shell-shaped configuration for the straddle-type usage of it;

FIG. 5 is a part plan view of the spaced coplanar arms of the tool before the implement is formed thereon;

FIG. 6 is a front elevational view of the arms at that time;

FIG. 7 is a part plan view of the arms when the implement has been formed thereon;

FIG. 8 is a cross sectional view of the arms and implement along the line 8—8 of FIG. 7;

FIG. 9 is a part cross sectional view along the same line, but enlarged to illustrate the pleat-like linkages in the flexible connections between the midsection and the wings of the implement;

FIG. 10 is a part plan view similar to that of FIG. 7, but wherein a differing form of pleat-like linkage is employed in the flexible connections;

FIG. 11 is a cross sectional view of the arms and implement along the line 11—11 of FIG. 10;

FIG. 12 is an enlarged part cross sectional view along that line, illustrating the differing form of linkage;

FIG. 13 is a cross section view similar to those of FIGS. 8 and 11, but wherein a third form of pleat-like linkage is employed;

FIG. 14 is a cross section view similar to those of FIGS. 8, 11 and 13, but wherein the arms of the tool and the wings of the implement are interengaged for relative rotation therebetween, and the leveraging means are formed in the flexible connections between the midsection and the wings of the implement;

FIG. 15 is a similar view when the implement has been reentrantly folded to activate the extensible and contractible toggle joint between the wings of the same;

FIG. 16 is a plan view of a tool wherein the arms of the tool and the wings of the implement are interengaged for relative rotation, but there are detents in the connections therebetween whereby the arms and wings can be fixed against relative rotation at angular intervals thereabout, the leveraging means being formed in the connections between the same at the respective intervals;

FIG. 17 is a cross sectional view of the arms of the tool in this embodiment;

FIG. 18 is a cross sectional view of the arms and implement in the same, when the implement is in the initial unfolded condition thereof;

FIG. 19 is a cross sectional view of the arms and implement along the line 19—19 of FIG. 16, when the implement is in the taco shell-shaped condition thereof for straddle-type usage of it;

FIG. 20 is a cross sectional view of a mold for making each of the tooth brushing implements in the various illustrated embodiments, when the implement has a monolithic cowling of resin material encased about the arms;

FIG. 21 is a similar cross sectional view of the mold when the resin material has been injected therein;

FIG. 22 is an enlarged cross sectional view of one bristle forming branch of the mold cavity, illustrating the technique by which the bristle are given a relatively harder core;

FIG. 23 is a partial but still greater enlargement of the branch seen in FIG. 22;

FIG. 24 is a perspective view of an apparatus for reentrantly folding the wings of the implement about the center section thereof, to give the implement a taco shell-shaped configuration for the straddle-type usage of it;

FIG. 25 is a front elevational view of the apparatus when the tool is positioned in the same for the folding operation;

FIG. 26 is a part cross sectional view of the apparatus when the tool has undergone the folding operation;

FIG. 27 is a top perspective view of a tool which has separate carrier means that are equipped with a pair of reversedly directed prongs for detachably engaging them with the distal end of the positioning means, at a pair of angularly related sockets therein which are adapted to preserve the taco shell-shaped configuration of the implement on the carrier means;

FIG. 28 is a top perspective view of the carrier means when the implement is in the initial unfolded condition thereof;

FIG. 29 is a cross sectional view of the tool along the line 29—29 of FIG. 27; and FIG. 30 is a part cross sectional, part schematic view of the tool when it has been modified to accommodate both the unfolded implement of FIG. 28 and the taco shell-shaped implement of FIG. 27.

BEST MODE FOR CARRYING OUT THE INVENTION

As indicated, each of the tools 2 seen in the drawings has a relatively unfolded pre-operative condition and a taco shell-shaped operative condition. Like those tooth brushing tools shown in the earlier Application, moreover, each comprises carrier means 4 which are adapted for insertion in the mouth of the user (not shown) and have an implement 6 thereon for brushing the teeth of the user. Each tool 2 also comprises elongated positioning means 8, including a handle 10, for supporting the carrier means 4 adjacent a row of the user's teeth while the implement 6 is applied thereto. The carrier means 4 comprise a pair of spaced, coplanar arms 12 that project from the distal end 14 of the positioning means 8 and are resiliently flexible in the plane of the arms at points 16 spaced outboard from the distal end of the positioning means. The implement 6 is supported on the arms 12 at the aforesaid points 16 and comprises a pair of spaced wings 18 and a midsection 20 in the space 22 (FIG. 8) therebetween, the wings 18 being relatively flexibly interconnected with the midsection 20 and having tooth brushing means 24 on corresponding sides thereof. The implement 6 is also interconnected with the respective arms 12 at the wings 18 thereof so that in the operative condition of the tool, the aforesaid tooth brushing sides 24 of the wings are opposed to one another in the space 26 (FIGS. 4 and 5) between the arms, and the midsection 20 of the implement 6 is supported on the wings 18, independent of the arms 12, to give the implement a taco shell-shaped configuration in which the wings 18 are capable of flexing in conjunction with the arms 12 at the connections 28 between the midsection 20 and the respective wings 18. In addition, there are leveraging means 30 in one of the pair of connections 32 between the arms 12 and the respective wings 18, and the pair of connections 28 between the midsection 20 and the respective wings 18, whereby when the implement 6 is straddled about the row of teeth and translated along the row opposite the inside and outside faces of the teeth, the implement retains the aforesaid configuration, yet the wings 18 of the same are capable of reciprocating in relation to one another crosswide of the space 26 between the arms to accommodate to variance in the diameter of the teeth.

As indicated earlier, it is desirable that the wings 18 maintain a predetermined angular relationship 33 (FIG. 4) therebetween when the undergo relative reciprocation in accommodating to variance in tooth diameter. Therefore, in accordance with the invention, each tool further comprises linkage means 34 (FIGS. 3 and 9) in the flexible connections 28 between the wings 18 and the midsection 20 whereby when the pairs of arms 12 and wings 18 reciprocate in conjunction with one another, crosswise of the space 26 between the arms, the midsection 20 responds to the reciprocation by reciprocating along perpendiculars to the plane of the arms to substantially preserve the angular relationship 33 between the wings. The linkage means 34 may be employed in a tool 2' in which the pairs of arms 12 and wings 18 are interlocked against relative rotation at the connections 32 therebetween (FIGS. 1-13), and in such a case, the leveraging means 30 are formed in the connections 32 between the arms and wings. Or the linkage means 34 may be employed in a tool 2" in which the pairs of arms and wings are interengaged for relative rotation at the connections 32 therebetween (FIGS. 14 and 15), and in that case, the leveraging means 30 are formed in the flexible connections 28 between the midsection 20 and wings 18 of the implement 6. Or, as seen in FIGS. 16-19, the linkage means 34 may be employed in a tool 2''' in which the arms and wings are interengaged for relative rotation at the connections 32 therebetween, but the rotary connections 32 have means 35 therein whereby the arms and wings can be fixed against relative rotation at angular intervals thereabout, the leveraging means 30 being formed in the rotary connections 32 at the respective intervals.

More particularly, the handle 10 of the tool 2' shown in FIGS. 1-9, has a lenticular cross section which is progressively more oblate in the direction of the distal end 14 of the positioning means 8, and there is a thumb-shaped swale 36 in the underside of the handle where, if desired, the user can place his thumb while he wraps is fingers about the handle 10 to position the carrier means 4 and implement 6 in his mouth. The carrier means themselves are cantilevered from the distal end 14 of the handle, and take the form of a reduced diameter boom-like extension 38 of the handle, which is more rectangular in cross section and bifurcated at the distal end portion 16 thereof to form juxtaposed halves that are resiliently flexible and separated from one another by a slot 40 to serve as the pair of arms 12. The arms 12 in turn have a pair of gusset-like brackets 42 thereon, which project to the sides of the arms, from the terminal end portions 16 thereof, and which in turn have clapper-shaped jaws 44 outriggered thereon, at the relatively forwardly oriented edges 46 thereof. In the pre-operative condition of the tool, the jaws 44 are coplanar with the brackets 42 and arms 12, and are cantilevered from the forwardly oriented edges 46 of the brackets at points 48 more widely spaced than the arms themselves, at their outboard edges 50, so that there is a considerable gap 26 between the jaws 44 at the forward end of the tool. The jaws 44 are also given a sweptback configuration along the forward edges 52 thereof, and sets of holes 54 and randomly distributed studs 56 are provided on the opposing sides of the jaws, for reasons which will be explained. Additionally, the jaws 44 are relatively thick, and the brackets 42 are relatively thin, so that when the tool 2' is put to use and the jaws are bent into a taco shell-shaped configuration for that purpose, bending will occur along bend-lines that extend generally parallel to the outboard edges 50 of the arms, and inside of the points 48 at which the jaws are cantilevered from the brackets. Moreover, to promote this effect still further, the bodies of the brackets 42 are ramped up to those of the jaws 44 at the edges 46 of the brackets, so that during the bending operation, the jaws are less likely to bend, relative to the brackets, than are the brackets relative to the arms. The ramps can be seen at 57.

The implement 6 is once again a casting, and through it might be precast and mounted on the arms 12 in the manner of the earlier Application, in this instance the implement 6 is cast directly on the jaws to have a monolithic hammock-like cowling 58 (FIGS. 7 and 8) of flexible and/or pliable sheet material which is rigidified in part by the jaws, but adapted so that it can be flexed and/or bent with the jaws into a taco shell-shaped configuration at the time of use. The cowling 58 has a relatively thin sheet-like body, which in turn has three successively flexibly interconnected sections 60, 62 and 64 therein, all of which have sea urchin-like field 60, 68 and 70 of individual bristle 72 upstanding on corresponding sides 74, 76 and 78 thereof. At the time of use, two of the fields, 66 and 70, are mutually opposed to one another on the wings 60 and 64 of the cowling, and the third field 68 is interposed between them, on the bight or midsection 62 of the same. Together, the three fields form an interdigitating "thicket" 24 of bristle that thoroughly engages each tooth when the implement 6 is straddled about a row of teeth in use. The fields 66, 70 on the wings 18 may also have pick-like bodies (not shown) therewithin, which can serve as stylii for tracing the gum lines of the row, as well as picks for removing debris from the same, but these are not shown, and reference should be made to the earlier Application for the details of the same.

In casting the implement, the three sections 60, 62 64 of the cowling are cast in a row crosswise of the jaw or application 44, and the wings 60, 64 of the cowling are cast around the jaws 44, so as to suspend the midsection 62 in the gap 26 therebetween. The three sections are cast in unison, moreover, and in addition to the midsection 62, webs 80 of thinner sheet material are also cast within the gap 26, to be supported with the midsection, trestle-like, between the respective wings 60, 64. The webs 80 are cast as reentrantly folded pleats of the thinner material, so that in use, the midsection and pleats form an extensible and contractible expansion joint 82 between the pairs of jaws and wings. Such a joint makes it possible for the respective pairs of jaws and wings to maintain a preset angular relationship 33 between the wings while the wings reciprocate in relation to one another to accommodate to variance in tooth diameter. Given arms 12 which are also resiliently flexible along perpendiculars to the plane of the arms at the points 16, the joint 82 also makes it possible for the respective pairs of jaws and wings to be reciprocated in opposite directions, relative to the plane of the arms, should the user wish to generate a vertical component to the cleaning action of the bristle. And in addition, if desired, the joint also makes it possible for the user to scrub each tooth, and the interstices between teeth, with certain of the criss-cross action discuss in the earlier Application.

Referring now to FIGS. 10–12, it will be seen that in lieu of being cast outside the plane of the cowling and reentrantly folded as pleats 80, the webs may be cast in the plane of the cowling as thin hinge lines 84 which have grooves 86 or other relief at one side thereof, and are perforated lengthwise thereof, as seen at 88 in FIG. 10, so as to give them the necessary extensibility and contractibility to perform like pleats, for example, in a children's tooth brush. Or in the alternative, where the cowling is cast from a suitable elastomeric material, the webs may be cast in the plane as thin hinge lines 90 which have relief on both sides thereof, as in FIG. 13, so as to be sufficiently stretchable to perform like pleats for the purposes of the invention.

In each of the tools 2 described thus far, the jaws 44 were substantially parallel to one another at the aforesaid points 48 thereon, the wings 18 were given substantially fixed angular orientations with the jaws, at the spigot and socket connections 32 therebetween, and the flexible connections 28 between the midsection 20 and the wings 18 included pleat-like linkages 34 therein whereby the midsection could reciprocate along perpendiculars to the plane of the arms to enable the wings to maintain the angular relationship 33 therebetween, when the pairs of jaws and wings reciprocated in conjunction with one another, crosswise of the space between the arms, to accommodate to variance in tooth diameter. In the case of the tool 2'' shown in FIGS. 14 and 15, however, the wings 92 are rotatable about the jaws 94, and the flexible connections 96 between the midsection 98 and the wings 92 include relatively articulated toggle links 100 therein whereby the midsection 98 reciprocates along perpendiculars to the plane of the arms, to rotate the wings 92 about the jaws 94, and thereby maintain the angular relationship between the wings when the pairs of jaws and wings reciprocate as indicated. In short, then, the midsection 98 and linkages 100 are employed as a toggle joint 102, rather than as an expansion joint 82 of the type which was used in the embodiments of FIGS. 1–13.

More particularly, the jaws 94 now have cylindrical bodies 104 which project, spigot-like, from the brackets (not shown) at the aforesaid points 48 thereon, and when the cowling 106 is cast about the jaws, the wings 92 prove to be rotatable on them, due to the fact that the casts form cylindrical sockets 108 about the jaws. Initially, the cowling assumes the bat-like, drop-wing configuration seen in FIG. 14, but when the tool is put to use, the wings 92 are rotated about the jaws 104 to the taco shell-shaped configuration of FIG. 15. This has the effect of elevating the midsection 98 to the position of FIG. 15, and in this position, the midsection will cooperate with the two links 100 in rotating the wings in the manner described, assuming that the links 100 have sufficient stiffness to perform as toggle links. That is, given links 100 of this stiffness, when the wings 92 are forced apart by a larger diameter tooth, and the jaws 104 reciprocate with them, the toggle joint 102 comprised of the links 100 and the midsection 98, will effectively rotate the wings through sufficient angular deflection to maintain the angle that was established between them when the cowling 106 was bent into the taco shell-shaped configuration of FIG. 15. Conversely, when the wings close about a tooth of narrower diameter, the joint 102 will toggle the wings in the opposite direction to once again maintain the angle therebetween.

It is also possible to provide a joint wherein the wings can be set at variable angles to one another, but when set, will maintain the angle therebetween because of the operation of an expansion joint 82 therebetween. Referring now to the tool 2''' shown in FIGS. 16-19, it will be seen that the jaws 110 of the arms 12 have axially extending flutes 114 thereon which are symmetrically arrayed about the axes of the jaws and rounded at the respective crests 116 and valleys 118 therebetween, so that given a sufficiently deformable material for the cowling 120, and a relatively non-deformable one for the jaws, such as relatively soft and hard plastic materials, respectively, the wings 112 can be rotated about the jaws from one flute 114 to the next, and when so rotated, the flutes will serve as detents for preserving the angular relationship between the wings during the use of the device as a toothbrush. When the device is out of use, however, the wings may be reset to some other angle, such as the relatively planar pre-operative condition seen in FIG. 18. Then, when the device is put back into sue again, they may be rotated once more to the taco shell-shaped configuration seen in FIG. 19.

Alternatively, the jaws 110 may be polygonal in cross-section, such as pentagonal, to provide detents at the corners of the their outlines.

Preferably, in all embodiments, the individual bristle 72 have a core of relatively harder material at the center thereof, and a sheath of relatively softer material surrounding the same. Also, the jaws, and in fact, the carrier and positioning means, are preferably constructed of one material, such as a relatively hard plastic material, and the cowling is constructed of another material which is softer than that of the jaws, such as a relatively softer plastic material.

Referring now to FIGS. 20-23, a process is shown for casting a plastic hammock-like cowling 58 around the jaws 44 of the arms 12 (FIGS. 1-13), and giving the cowling monolithic bristle 72 which have relatively harder cores surrounded by the softer plastic material of the cowling itself. According to the process, jaws 44 of relatively high melting temperature plastic resin are clamped between a pair of relatively reciprocable mold cavity-forming members 122, 123, the opposing faces 124, 125 of which have recesses 126, 128 therein that complement one another in forming cavities 130 that correspond to the bodies of the wings 60, 64 when the recesses 126, 128 are registered with one another as shown. When the jaws are so clamped, however, the studs 56 of the jaws abut the members, so that interstitial spaces 132 remain among the studs on each side of the cavities, to allow molten, relatively low melting temperature plastic resin to be introduced around the jaws, on all sides thereof. The cavities 130 are interconnected, meanwhile, by an intermediate cavity (not shown) corresponding in size and shape to the body of the midsection 62 of the cowling, as well as to the bodies of the webs 80 interconnecting it with the wings 60, 64. In addition, at what is to become the inside faces 74, 76, 78 of the wings and midsection, there are conical branches 134 which are recessed into the adjacent member 123 on perpendiculars to the face 125 thereof, and the branches 134 which are recessed into the at the tips thereof for the escape of gas from the cavities 130 of the mold. The branches 134 form the bristle 72 for the tooth brushing means 24 on the corresponding sides of the wings and midsection, and preferably an electric discharge machine is used to form the branches themselves so that the walls 138 of the branches are knurled to provide texture for the bristle formed therein.

Injection ports 140 are provided for the respective cavities 130, as well as the intermediate cavity, and in the process the relatively low melting temperature plastic resin is injected into the cavities to flow about the sets of studs 56 and to fill the cavities with resin, including the holes 54 therebetween. The resin also flows into the branches 134, to charge them as well, and as it does, any gas entrained in the resin escapes through the ports 136 at the tips of the branches. Throughout the operation, moreover, elongated rods 142 of a harder high melting temperature resin are added to the molten resin, to be introduced to the respective branches with the resin, as shown in FIGS. 22 and 23. Because of their length, and because of the fluid mechanics of the flow, the rods 142 tend to orient directionally of the flow, and at the center of the mass thereof in each branch. The rods 142 also remain solid in the molten mass, and agglomerate down the centers of the branches 134, where they closely compact with one another and become elongated stems of harder material at the cores of the bristle formed in the branches.

Commonly, a hard plastic resin with a melting temperature of about 600° F. is used in the jaws 44 themselves, and a softer resin with a melting temperature of about 225° F. is used in forming the cowling 58 about the jaws. Examples of suitable resin materials are given in the earlier Application and include certain polycarbonates, such as General Electric's Lexan brand of polycarbonates, for the frame 4, 8, 12 of each tool, and certain thermoplastic elastomers, such as ethyl vinyl acetate, for the cowling 58.

Commonly, the cowling 58 is made up as a planar substrate having the bristle 72 perpendicularly outstanding thereon, and in addition, at varying lengths on the wings 60, 64 thereof, so that the fields 66, 70 have oppositely inclined profiles at the tips 142 thereof, relative to the dimensional plane of the substrate at the midsection 62 thereof. There may also be stylus-like means upstanding in the bristle on the wings, as seen at 144 in FIGS. 14 and 15, and once again, as in the earlier Application, the stylus-like means may be made semirigid to perform as picks. The picks may also have barbs 145 at the ends thereof, to aid in their function as such.

As was also described in the earlier Application, and is seen in FIG. 14, the substrate may be given a drop wing configuration in which the wings 92 are obliquely angled to the plane of the midsection at, say, 165 to each side thereof.

Substrates such as those made up for the embodiments of FIGS. 14 and 15, and FIGS. 16-19, are commonly positioned in the cavity by sets of retractable pins (not shown), inserted for example, between the branches 134 of the member 123 on that side of the cavity, and through the member 122 on the other side thereof.

The substrate may be reentrantly folded into a generally U-shaped configuration using, for example, the device illustrated in FIGS. 24-26. The device comprises a pair of rotary platens 146 and 148, and a pair of clamps 150 and 152 with which to secure the tooth brushing device 2 in position on the platens while they are rotated in relation to one another to reentrantly fold the wings 18 about the midsection 20, as seen in FIG. 26. The platens 146, 148 are rotatably mounted on a pair of spaced parallel shafts 154, and they have adjoining saddles 156 recessed therein, crosswise of the shafts, to receive the head 6, 44 of the brushing device as shown. The lower clamp 150, meanwhile, is stationary and has a keyway 158 upstanding along the center thereof, in line with the vertical plane dividing the pair of platens. The keyway 158 is adapted to insert within the slot 40 between the arms, and the upper clamp 152 is reciprocably mounted to be lowered into clamping engagement with the arms 12 when they are straddled about the keyway 158 to rest the head 6, 44 on the pair of saddles 156 of the platens. In addition, the platens 146, 148 are rounded at the adjacent corners 160 thereof, so that they can be rotated inward of one another in the manner seen in FIG. 26, using a pair of handles 162 that project from the outsides thereof. As the platens are rotated, the upper sides 164 of the saddles 156 abut the wings 60, 64 of the substrate, as well as the brackets 42 of the arms 12, and bend the same into an angle 33 adapted to provide the gap needed between the wings for use of the device as a straddle-type tooth brush.

Alternatively, the carrier means and implement alike may be bent into the desired U-shaped configuration by the technique seen in FIGS. 27-30. The carrier means 166 and implement 6 are manufactured as a separate assembly 168 in which there is a pair of prongs 170 having the arms 12 as extensions thereof, as seen in FIG. 28. Meanwhile, the handle 10 of the positioning means 8, has a bifurcated extension 172, the two portions 174 of which provide sockets 176 for the prongs 170 of the assembly. The sockets 176 are rectangular in cross section and angled toward one another at the same angle 33 as that needed between the wings 18 of the assembly. When the prongs 170 are rotated to that angle, to give the implement the U-shaped configuration seen in FIG. 27, the prongs 170 may then be bayoneted into the sockets 176 of the extension 172 to render the device ready for use, the prongs, meanwhile, forcibly engaging in the sockets 176 to tightly secure the assembly to the positioning means 8 at the required angle.

In still another version, the extension 172 of the handle is equipped with two pairs of sockets 176, 178, one of which, 178, is coplanar to receive the pronged ends 170 of the assembly 168 when it is in the unfolded condition thereof, and the other pair of which, 170, is angularly related to receive the pronged ends of the assembly when it is bent into the U-shaped condition thereof. Such a version is especially suited to the marketing of the brush in the most compact form, i.e., the condition of FIG. 28, whereafter the assembly 168 is removed from the sockets 178, bent into the taco shell-shaped condition, and then reinserted in the sockets 170 to render it useful as a straddle-type tool.

I claim:

1. In the manufacture of a tooth brush having an arm at the head thereof, and an applicator on the outboard end portion of the arm, having tooth cleaning bristles on one side thereof, the steps of:

positioning the arm in a plane, enclosing the outboard end portion of the arm in a mold cavity which is defined by the mutually opposing faces of a pair of relatively reciprocable members on opposing sides of the plane, and has a cross section corresponding to the body of the applicator, one of the mold cavity defining members having elongated bristle defining branches therein which extend transverse the plane of the arm and open into the face of the one member at the cavity, interposing spacer elements between the outboard end portion of the arm and the faces of the members on the opposing sides of the plane to substantially surround the outboard end portion of the arm with unoccupied portions of the cavity, injecting a mass of plastic resin material into the unoccupied portions of the cavity to substantially encircle the outboard end portion of the arm with said material, and venting the gas in the cavity through the branches of the same when the resin mass substantially encircles the outboard end portion of the arm and charges into the branches to form a plastic monolith comprising the applicator having bristles relatively upstanding on one side thereof.

2. The method according to claim 1 wherein the spacer elements take the form of spaced studs upstanding on the outboard end portion of the arm transverse the plane of the arm.

3. The method according to claim 1 wherein the plastic resin material is injected into the cavity along parallels to the plane of the arm.

4. The method according to claim 1 wherein the walls of the branches have means thereon for texturing the exterior surfaces of the bristles.

5. The method according to claim 1 wherein the gas is vented at the tips of the branches.

6. The method according to claim 5 wherein the branches are tapered relatively inwardly of the longitudinal axes thereof, in the direction generally outwardly of the cavity, and the method further comprises entraining elongated rods of a relatively higher melting temperature resin material in the mass of resin material charged into the branches when the gas is vented at the tips of the same, to form cores of the relatively higher melting temperature resin material along the longitudinal axes of the bristles.

7. The method according to claim 1 wherein the arm is elongated and projects relatively outboard from the distal end of a handle for the tooth brush.

* * * * *